United States Patent [19]

Greenquist et al.

[11] 4,442,204
[45] Apr. 10, 1984

[54] HOMOGENEOUS SPECIFIC BINDING ASSAY DEVICE AND PREFORMED COMPLEX METHOD

[75] Inventors: Alfred C. Greenquist, Elkhart; Bert Walter, South Bend, both of Ind.

[73] Assignee: Miles Laboratories, Inc., Elkhart, Ind.

[21] Appl. No.: 253,147

[22] Filed: Apr. 10, 1981

[51] Int. Cl.³ .................. G01N 33/54; G01N 33/58; G01N 33/52
[52] U.S. Cl. .................. 435/7; 422/56; 422/57; 435/805; 436/518; 436/530; 436/537; 436/810; 436/815
[58] Field of Search .......... 435/4, 7, 805, 810; 23/230 B; 424/8, 12; 422/52, 55, 56; 436/514, 515, 516, 531, 532, 536, 537, 538

[56] References Cited

U.S. PATENT DOCUMENTS

| | | | |
|---|---|---|---|
| 3,979,184 | 9/1976 | Giauer | 435/7 |
| 4,056,407 | 11/1977 | Hochstrasser | 435/7 |
| 4,094,647 | 6/1978 | Deutsch et al. | 435/7 |
| 4,226,978 | 10/1980 | Boguslaski et al. | 435/7 |
| 4,238,565 | 12/1980 | Hornby et al. | 435/7 |
| 4,258,001 | 3/1981 | Pierce et al. | 435/7 |
| 4,275,149 | 6/1981 | Litman et al. | 435/7 |
| 4,277,560 | 7/1981 | Gray et al. | 435/7 |
| 4,279,992 | 7/1981 | Boguslaski et al. | 435/7 |
| 4,299,916 | 11/1981 | Litman et al. | 435/7 |
| 4,318,981 | 3/1982 | Burd | 435/7 |
| 4,323,647 | 4/1982 | Monji | 435/7 |
| 4,362,697 | 12/1982 | Tabb et al. | 422/56 |
| 4,363,874 | 12/1982 | Greenquist | 422/56 |
| 4,366,241 | 12/1982 | Ton et al. | 422/56 |
| 4,366,243 | 12/1982 | Rupchock et al. | 435/7 |
| 4,391,904 | 7/1983 | Litman | 422/56 X |

*Primary Examiner*—Sidney Marantz
*Attorney, Agent, or Firm*—Edward H. Gorman, Jr.

[57] ABSTRACT

A homogeneous specific binding assay device, a method for its preparation, and a method for its use in determining a ligand, such as antigen, hapten, or antibody, in a liquid sample. The test device comprises a solid carrier member, such as a fibrous web matrix, e.g., paper, or a polymeric film or gel, incorporated with reagents for a homogeneous specific binding assay system which produces a detectable response, usually an electromagnetic radiation signal, that is a function of the presence or amount of the ligand in the sample. For example, disclosed is a test device for determining a ligand in a liquid sample, comprising (a) a reagent composition including a complex of (i) a labeled conjugate comprising a label component coupled to said ligand or a specific binding analog thereof, and (ii) a specific binding partner for said ligand, said label providing a detectable response, or interacting with a detectant system to provide a detectable response, which is different when the labeled conjugate is bound by said binding partner compared to when it is not so bound, whereby the detectable response is a function of the presence of the ligand in the sample, and (b) a carrier incorporated with said complex. Useful homogeneous specific binding assay systems include those involving enzyme substrate labels, enzyme prosthetic group labels, and enzyme labels. The detectable response preferably is a luminescent, fluorescent, spectrophotometric, or colorimetric response, which is measurable by visual observation or instrument means.

13 Claims, 8 Drawing Figures

DRUG IMMUNOASSAY

I. ENZYMATIC REACTION

II. ANTIBODY BINDING REACTION

III. COMPETITIVE BINDING REACTION

DRUG IMMUNOASSAY
I. ENZYMATIC REACTION
II. ANTIBODY BINDING REACTION
III. COMPETITIVE BINDING REACTION
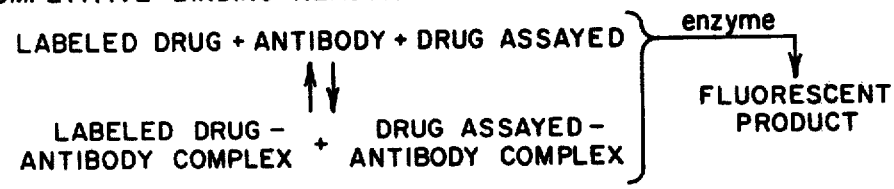
FIG. I

HOMOGENEOUS SPECIFIC BINDING ASSAY DEVICE AND PREFORMED COMPLEX METHOD

BACKGROUND OF THE INVENTION

1. Field of the Invention

This invention relates to test devices, their preparation and their use in determining a ligand in a liquid sample based on a specific binding assay, e.g., immunoassay, principle. In particular, this invention relates to solid state carrier elements incorporated with homogeneous specific binding assay reagents.

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease.

Test strips of various types have been known and used for many years in a wide variety of fields, from the most familiar pH test paper devices to in vitro diagnostic devices for the detection of various urine and blood components such as glucose, protein, occult blood and so forth (e.g., as described in U.S. Pat. Nos. 3,164,534; 3,485,587; and 3,012,976). Reagent compositions found in such conventional test strips, having limited sensitivity, interact with the constituent or constituents to be determined by direct chemical reaction and are applied to the detection of substances that are present in liquid samples at concentrations in the millimolar range or above.

On the other hand, the development of specific binding assay techniques has provided extremely useful analytical methods for determining various organic substances of diagnostic, medical, environmental and industrial importance which appear in liquid mediums at very low concentrations. Specific binding assays are based on the specific interaction between the ligand, i.e., the bindable analyte under determination, and a binding partner therefor. Where one of the ligand and its binding partner is an antibody and the other is a corresponding hapten or antigen, the assay is known as an immunoassay.

In conventional specific binding assay techniques, a sample of the liquid medium to be assayed is combined with various reagent compositions. Such compositions include a labeled conjugate comprising a binding component incorporated with a label. The binding component in the labeled conjugate participates with other constituents, if any, of the reagent composition and with the ligand in the medium under assay. This forms a binding reaction system in which two species, a bound-species and a free-species, of the labeled conjugate are formed. In the bound-species, the binding component of the labeled conjugate is bound by a corresponding binding partner, e.g. an antibody, whereas in the free-species, the binding component is not so bound. The relative amount or proportion of the labeled conjugate that results in the bound-species compared to the free-species is a function of the presence (or amount) of the ligand to be detected in the test sample.

Where the labeled conjugate in the bound-species is essentially indistinguishable in the presence of the labeled conjugate in the free-species by the means used to monitor the label, the bound-species and the free-species must be physically separated in order to complete the assay. This type of assay is referred to in the art as "heterogeneous". Where the bound-species and free-species forms of the labeled conjugate can be distinguished in the presence of each other, the separation step can be avoided, and the assay is said to be "homogeneous".

The first discovered type of highly sensitive specific binding assay was the radioimmunoassay which employs a radioactive isotope as the label. Such an assay necessarily must follow the heterogeneous format since the monitorable character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g., an electromagnetic radiation signal, such as chemiluminescence, fluorescence emission, or color change, related to the presence of amount of the ligand under assay in the liquid sample.

Commercially available test means for performing specific binding assays are usually in the form of test kits comprising a packaged combination of containers holding solutions or rehydratable compositions of the reagents necessary for carrying out the assay. To perform the actual assay method, aliquots of such solutions must be manually or instrumentally dispensed into a reaction vessel with the sample. If manually dispensed, the assay consequently requires the time and skill of a technician, and if instrumentally dispensed, the assay consequently requires the expense and maintenance of dispensing apparatus.

2. Brief Description of the Prior Art

Solid phase tests devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4,105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluoroescent immunoassays (U.S. Pat. Nos. 4,025,310 and 4,056,724; and British Pat. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with the remaining reagents of the reaction system, principally the labeled conjugate. After an incubation period, the solid phase device is physically removed from the reaction solution and the label measured either in the solution or on the test device.

Similar devices where the antibody reagent is entrapped in a matrix such as a gel or paper web are described in U.S. Pat. Nos. 3,925,017; 3,970,429; 4,138,474; 3,966,897; 3,981,981 and 3,888,629 and in German OLS No. 2,241,646. Likewise, devices for use in heterogeneous specific binding assays wherein the antibody reagent is fixed to a matrix held in a flowthrough column are known (U.S. Pat. Nos. 4,036,947; 4,039,652; 4,059,684; 4,153,675; and 4,166,102). The test device is usually incorporated with less than all of the necessary reagents for carrying out the assay and is merely a means for rendering more convenient the necessary separation step.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay. Yet another approach to a heterogeneous immunoassay element is exemplified by U.S. Ser. No. 973,669, published as European Patent Application No. 0 013 156.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as required when using the prior art test kits. Solid state devices would also be much more adaptable to automation than the prior art liquid systems.

British Pat. No. 1,552,607, commonly assigned herewith, describes homogeneous specific binding assay systems employing various novel labels, including chemiluminescent labels, enzyme substrate labels and coenzyme labels. At page 23, lines 12 et seq of this patent there is the suggestion to incorporate the assay reagents with various carriers including liquid-holding vessels or insoluble, porous, and preferably absorbent, matrices, fleeces, or flocks; gels; and the like. This lacks a detailed teaching of how to apply homogeneous specific binding assay reagent systems to solid state test devices.

German OLS No. 2,537,275 describes a homogeneous specific binding assay reagent system and poses the possibility of using slides or strips incorporated with antibody in performing the assay. In this suggestion, the labeled conjugate would be first mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element with the labelled conjugate being separately added to the sample under assay prior to contact with the proposed test device.

Copending U.S. Ser. No. 202,378, filed on Oct. 30, 1980 and commonly assigned herewith, discloses a homogeneous specific binding assay device, a method for its preparation, and a method for its use in determining a ligand, such as antigen, hapten, or antibody, in, or the ligand binding capacity of, a liquid sample. This includes, for example, a test device for determining a ligand in or the ligand binding capacity of a liquid sample, comprising (a) reagents for a homogeneous specific binding assay system which produces a detectable response that is a function of the presence of the ligand in or the ligand binding capacity of the sample, and (b) a solid carrier member incorporated with said reagents.

SUMMARY OF THE INVENTION

The present invention provides a homogeneous specific binding assay test device, a method for its preparation, and a method for its use in determining a ligand in a liquid sample. The test device comprises (a) reagents for a homogeneous specific binding assay system which produces a detectable response that is a function of the presence, in a qualitative or quantitative sense, of the ligand in the liquid sample under assay, and (b) a solid carrier member incorporated with such reagents. The carrier member is preferably a matrix which is absorbent relative to the liquid sample, such as web matrix composed primarily of natural or synthetic polymer fibers, e.g., paper, or a polymeric film or gel, such as used in multilayer elements.

Competition between sample ligand and labeled ligand for binding to a binding partner (here exemplified by an antibody-"Ab") can be summarized by the equation:

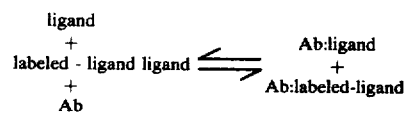

In the system illustrated above, the antibody and the labeled-ligand are kept separate until the introduction of the sample. In contrast, the described invention makes use of the reverse reaction and reequilibration with the ligand as shown by the equation below:

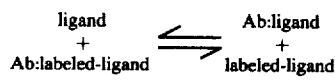

where the amount of displaced labeled ligand is related to the sample ligand concentration. The advantage is that all reagent components can be combined in one incorporation medium to provide a device or element that requires only the addition of sample to be tested.

In accordance with the invention, the method of preparing a device for determining a ligand in a liquid sample comprises forming a complex between a labeled conjugate, said conjugate comprising a label component coupled to said ligand or a specific binding analog thereof, and a specific binding partner for said ligand; and incorporating a carrier with said complex. For a preferred embodiment, forming said complex comprises associating said conjugate and specific binding partner therefor and allowing the conjugate, the binding partner and the complex to reach equilibrium. This equilibrium can be such that substantially all of said conjugate is complexed.

In use, the test device is contacted with the liquid sample, e.g., a biological fluid such as serum or urine, such as by momentarily immersing the reagent incorporated carrier member in the sample or by dispensing an aliquot of the sample onto a surface of the carrier member. The detectable response is thereafter measured, usually after a predetermined incubation or reaction period, either by observation of the individual performing the assay or by instrument means. The detectable response is most commonly an electromagnetic radiation signal, for example, fluorescence, chemiluminescence, color changes and spectrophotometric responses.

Preferred homogeneous specific binding assay systems are those known in the art which involve a label which participates in an enzymatic reaction. One such preferred assay system is that wherein the label is an enzyme prosthetic group and wherein the extent to which an apoenzyme is able to combine with such prosthetic group label to form an active holoenzyme is dependent on the presence of the ligand or binding capacity therefor. The holoenzyme can be measured by its enzymatic activity according to a wide variety of schemes, including colorimetric schemes. Another preferred assay system is that wherein the label is an enzyme substrate and wherein the extent to which an enzyme is able to act on such substrate label to produce a detectable product is dependent on the presence of the ligand or binding capacity therefor. In such a homogeneous specific binding assay system, the detectable product is preferably fluoresence whereby the detectable response from the test device is measurable by a fluorometer. Also useful as the homogeneous specific binding assay system is that wherein the label is an enzyme and wherein the activity of such enzyme label is dependent on the presence of the ligand or binding capacity therefor. In this case also, enzyme activity can be measured in a wide variety of ways.

BRIEF DESCRIPTION OF THE DRAWINGS

FIGS. 1-8 are graphical representations of procedures used in and data obtained from the experiments described in the examples below.

DESCRIPTION OF THE PREFERRED EMBODIMENTS

Figure 2:
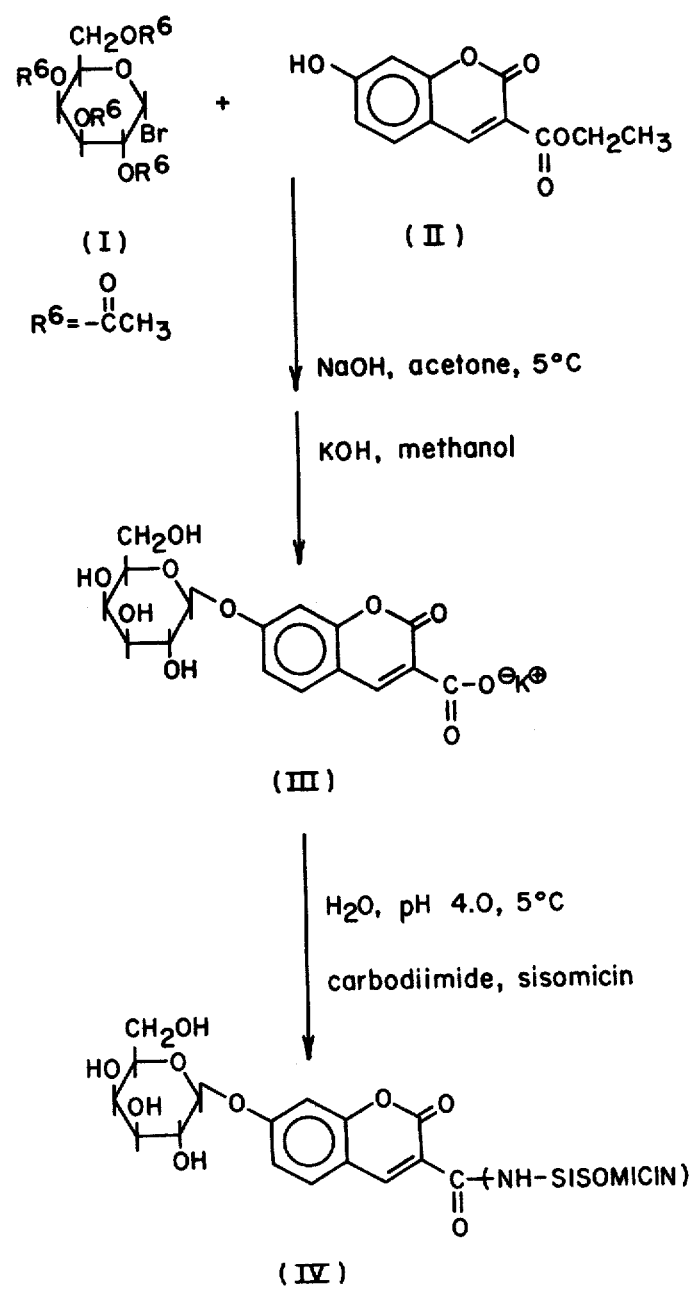

The present invention provides a test device for use in carrying out homogeneous specific binding assays, e.g., immunoassays, having all of the convenience features of conventional analytical test strips and other test elements of similar design. As in the case of such conventional devices, the present invention provides a solid carrier, usually a matrix of one sort or another, incorporated with all of the reagents necessary to perform a given assay whereby the user has only the task of bringing the test device into contact with the sample to be tested and measuring the resulting response. Where the entire process is automated, an instrument for performing the same manipulations can have a much simpler design than one having to deal with conventional liquid chemistry systems now used for performing homogeneous specific binding assays.

HOMOGENEOUS SPECIFIC BINDING ASSAYS

Reagents for any homogeneous specific binding assay system may be incorporated in the present test device. In general, homogeneous specific binding assay techniques are based on the special interaction between (1) a conjugate of a binding component and a label and (2) a binding partner to the binding component in the conjugate, whereby a characteristic of the label is different when the labeled conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristic is a physical characteristic of the label which can be measured without chemical reaction.

In the majority of cases, the present test device will incorporate homogeneous specific binding assay reagents which interact with the ligand in the sample in an immunochemical manner. That is, there will be an antigen-antibody or hapten-antibody relationship between reagents and/or the ligand or its binding capacity in the sample. Such assays therefore are termed immunoassays and the special interaction between the labeled conjugate and its binding partner is an immunochemical binding. Thus, in such instances, the binding component of the labeled conjugate is an antigen, hapten or antibody (or a fragment thereof) and the binding partner is its corresponding immunochemical binding partner. However, it is well understood in the art that other binding interactions between the labeled conjugate and the binding partner serve as the basis of homogeneous specific binding assays, including the binding interactions between hormones, vitamins, metabolites, and pharmolocgical agents, and their respective receptors and binding substances.

Where the sample is being assayed to determine the presence or amount of a particular ligand therein, the reagents for the homogeneous specific binding assay technique comprise, in the usual case, (1) a labeled conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the labeled conjugate. A limiting amount of the binding substance is introduced so that any ligand in the sample will compete with the labeled conjugate for binding to the binding partner. The distribution of the label between the bound-species and the free-species will therefore determine the magnitude of the detectable response from the label, which in turn will be a function of the presence of the ligand. Another scheme for determining a ligand is presented where the labeled conjugate is composed of a labeled binding partner of the ligand and upon binding to the ligand the label is affected in terms of its detectable response.

Several different homogeneous specific binding assay systems are known in the art, and the following are examples, without limiting the scope of the present invention, of some such systems contemplated for use in the present test device. The following systems are listed according to the nature of the label used.

1. Enzyme prosthetic group labels

In this system, where the label is a prosthetic group of an enzyme, the ability of a catalytically inactive apoenzyme to combine with the prosthetic group label to form an active enzyme (holoenzyme) is affected by binding of the labeled conjugate with its binding partner. Resulting holoenzyme activity is measurable by conventional detectant systems to yield an ultimately detectable signal. Assay systems of this type are described in commonly assigned U.S. Pat. No. 4,238,565. A particularly preferred prosthetic group-labeled assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide.

In such preferred assay scheme, the FAD-labeled conjugate is preferably of the formula:

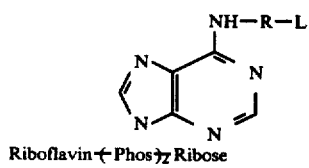

Riboflavin–(Phos)₂–Ribose wherein Riboflavin-(Phos)₂-Ribose represents the riboflavin-pyrophosphate-ribose residue in FAD, R is a linking group, and L is the binding component, e.g., the ligand or analog thereof.

2. Enzyme substrate labels

In this system, the label is selected so that the labeled conjugate is a substrate for an eyzyme and the ability of the enzyme to act on the substrate-labeled conjugate is affected, either in a positive or negative sense, by binding of the labeled conjugate with its binding partner. Action of the enzyme on the substrate-labeled conjugate produces a product that is distinguishable in some feature, usually a chemical or physical feature such as chemical reactivity in an indicator reaction or such as a photometric character, e.g., fluoroescence or light absorption (color). Assay systems of this type are described in commonly assigned U.S. Pat. No. 4,226,978, copending applications Ser. Nos. 894,836, filed Apr. 10 ,1978 (corresponding to published German OLS 2,618,511) and 87,819, filed Oct. 23, 1979; and in *Anal. Chem.* 48:1933 (1976), *Anal. Biochem.* 77:55 (1977) and *Clin. Chem.* 23:1402 (1977). A particularly preferred substrate-labeled assay scheme employs a labeled conjugate of the structure

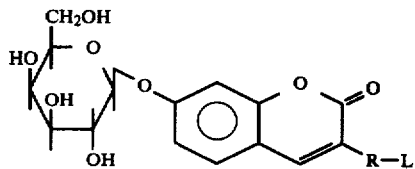

wherein R is a linking group and L is the binding component, e.g., the ligand or analog thereof, whereby the ability of the enzyme β-galactosidase to cleave the conjugate yielding a product distinguishable by its fluorescence is inhibited by binding of the conjugate with its binding partner.

3. Coenzyme labels

The labeled conjugate in this system is composed, in its label portion, by a coenzyme-active functionality, and the ability of such coenzyme label to participate in an enzymatic reaction is affected by binding of the labeled conjugate with its binding partner. The rate of the resulting enzymatic reaction is measurable by conventional detectant systems to yield an ultimately detectable signal. Assay systems of this type are described in commonly assigned, copending application Ser. No. 894,836, filed Apr. 10, 1978 (corresponding to published German OLS 2,618,511); and in *Anal. Biochem.* 72:271 (1976), *Anal. Biochem.* 72:283 (1976) and *Anal. Biochem.* 76:95 (1976).

4. Enzyme modulator labels

The labeled conjugate in this system is composed, in its label portion, of an enzyme modulating functionality such as an enzyme inhibitor or stimulator, and the ability of such modulator label to modulate the activity of an enzyme is affected by binding of the labeled conjugate with its binding partner. The rate of the resulting enzymatic reaction is measurable by conventional detectant systems to yield an ultimately detectable signal. Assay systems of this type are described in commonly owned U.S. Pat. No. 4,134,792.

5. Enzyme labels

In this system, the label is an enzyme and the activity of the enzyme label is affected by binding of the labeled conjugate with its binding partner. Resulting enzyme activity is measurable by conventional detectant systems to yield an ultimately detectable signal. Assay systems of this type are described in U.S. Pat. Nos. 3,817,837 and 4,043,872.

6. Quenchable fluorescent labels

The labeled conjugate in this system is composed, in its label portion, of a fluorescer whose fluorescence is quenched in some measurable degree when the labeled conjugate is bound by its binding partner, usually a protein such as an antibody. The fluorescent label is measured directly, with its fluorescence being the detectable signal. Assay systems of this type are described in U.S. Pat. No. 4,160,016 and in *J. Clin. Path.* 30:526 (1977).

7. Chemically-excited fluorescent labels

In this system, the label is again a fluorescer, however, the ability of the fluorescer label to be chemically excited to an energy state at which it fluoresces is affected by binding of the labeled conjugate with its binding partner. Chemical excitation of the label is usually accomplished by exposure of the fluorescer label to a high energy compound formed in situ. Assay systems of this type are described in commonly-owned U.S. Pat. No. 4,238,195.

8. Double antibody steric hindrance labels

Another assay system is the double antibody immunoassay system described in U.S. Pat. Nos. 3,935,074 and 3,998,943. The labeled conjugate comprises two epitopes, one of which participates in the immunological reaction with the ligand and antiligand antibody and the other of which is bindable by a second antibody, with the restriction that the two antibodies are hindered from binding to the labeled conjugate simultaneously. The second epitope can be a fluorescent substance whose fluorescence is quenched by the second antibody binding, or may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in British Pat. Spec. No. 1,560,852.

9. Energy transfer labels

In this system, the label is one member of an energy transfer donor-acceptor pair and the binding partner is conjugated with the other of such pair. Thus, when the labeled conjugate is bound by binding partner, the energy expression of the donor component of the pair is altered by transference to the acceptor component. Usually, the donor is a fluorescer and the acceptor is a quencher therefor, which quencher may or may not be a fluorescer as well. In such embodiment, the detectable signal is fluorescence, but other detectant systems are possible also. Such assay systems are described in U.S. Pat. Nos. 3,996,345; 4,174,384; and 4,199,559 and in British Pat. Spec. No. 2,018,424.

10. Other labels

Other homogeneous specific binding assay systems described in the art which can be used in the present invention include the use of such labels as:
(a) nonenzymic catalysts, such as electron transfer agents (see U.S. Pat. No. 4,160,645);
(b) nonenzymic chemiluminescers (see commonly owned, copending application Ser. No. 894,836 referred to above);
(c) "channeling" labels (see British Pat. Spec. No. 2,018,986);
(d) "particle" labels (see British Pat. Spec. No. 2,019,562); and
(e) labeled liposome particles (see U.S. Pat. No. 4,193,983).

LIGAND

The present assay may be applied to the detection of any ligand for which there is a specific binding partner. The ligand usually is a peptide, polypeptide, protein, carbohydrate, glycoprotein, steroid, nucleic acid, polynucleic acid sequence or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, interferon, human serum albumin, $\alpha_1$-glycoprotein, transcortin, thyroxine binding globulin, haptoglobin, hemoglobin, myglobin, ceruloplasmin, $\alpha_2$-lipoprotein, $\alpha_2$-macroglobulin, $\beta$-lipoprotein, erythropoietin, transferrin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogeanse, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as heptatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilimicin, penicillin, tetracycline, terramycin, chloromycetin, and actinomycetine; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepine, doxorubicin, nortryptiline, methotrexate, imipramine, lidocaine, procainamide, N-acetyl-procainamide, the amphetamines, the catecholamines, and the antihistamines.

The liquid medium to be assayed can be a naturally occurring or artifically formed liquid suspected to contain the ligand, and usually is a biological fluid or a dilution thereof. Biological fluids that can be assayed include serum, plasma, urine, saliva, and amniotic and cerebrospinal fluids.

CARRIER MEMBER

The carrier member of the present invention can take on a multitude of forms, and is therefore intended as being broad in context. It can be mono- or multi-phasic, comprising one or more appropriate materials or mediums of similar or different absorptive or other physical characteristics. It can be hydrophobic or hydrophilic, bibulous or nonporous. In its most efficient embodiment the carrier member can be carefully tailored to suit the characteristics of the particular homogeneous specific binding assay system to be employed.

Thus, as used herein, the term "carrier member" can comprise any substance, matrix, or surface capable of being incorporated with specific binding assay reagents. It can take on many known forms such as those utilized for chemical and enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of papers is suggested in British Pat. No. 1,369,139. Another British Patent, No. 1,349,623, suggests the use of a light-permeable meshwork of thin filaments as a cover for an underlying paper carrier element. This reference also suggests impregnating the paper with part of a reagent system and impregnating the meshwork with other potentially incompatible chemical or enzymatic reagents. French Pat. No. 2,170,397 teaches the use of carrier members having greater than 50% polyamide fibers therein. Another approach to carrier members is disclosed in U.S. Pat. No. 4,046,513 wherein the concept of printing reagents onto a suitable carrier is employed. U.S. Pat. No. 4,046,514 discloses the interweaving or knitting of filaments bearing reagents in a reactant system. All such carrier member concepts can be employed in the present invention, as can others. Preferably the carrier member comprises a bibulous material, such as filter paper, whereby a solution or suspension of the reagents of the specific binding assay system is used to impregnate the carrier member. It can also comprise a system which physically entraps these ingredients, such as in polymeric microcapsules, which then rupture upon contact with the test sample. It can comprise a system wherein the ingredients are homogeneously combined with the carrier member in a fluid or semi-fluid state, which later hardens or sets, thereby entrapping the ingredients.

Whichever material is chosen for the carrier member, whether it be porous to permit incorporation of ingredients such as thorough saturation with a solution containing them, whether it be nonporous such as for use in printed application of reagents or to support a continuous coating, whether it be woven or knitted, whatever its composition or configuration, its selection will in any event be dictated by anticipated use and by the reagent system.

For example, the system is prepared by first preincubating the antibody and the conjugate for the detection of a specific ligand. The ratio of available antibody binding sites to available conjugate is preferably 1:1. The complex is allowed to preform, usually requiring a duration not longer than about fifteen minutes. At the end of this period, any additional reagents which might be necessary such as an enzyme (e.g., β-galactosidase), are added to the solution. For a quenching system the introduction of additional reagents would not be necessary. The solution is then applied to a carrier and this is allowed to set. This is then cut into the appropriate geometry to provide analytical elements.

Where the carrier member comprises multiple layers, e.g., paper or other fibrous material, such layers may be maintained in laminar relationship by adhesives which permit fluid passage between layers. In preparing integral analytical elements using film formers, the layer(s) can be preformed separately and laminated to form the overall element. The material of the film layer(s) can be a composition comprising a plasticizer and a polymer suitable to impart dimensional stability. Layers prepared in such a manner are typically coated from solution or dispersion onto a surface from which the dried layer can be physically stripped. However, a convenient method which can avoid problems of multiple stripping and lamination steps is to coat an initial layer on a stripping surface or a support, as desired, and therafter to coat successive layers directly on those coated previously. Such coating can be accomplished by hand, using a blade coating device, or by machine, using techniques such as dip or bead coating. If machine coating techniques are used, it is often possible to coat adjacent layers simultaneously using hopper coating techniques as well known in the preparation of light sensitive photographic films and papers.

Blush polymer layers can be used as the film layer material. The film is formed on a substrate by dissolving a polymer in a mixture of two liquids, one of which is of a lower boiling point and is a good solvent for the polymer and the other of which is of a higher boiling point and is a nonsolvent or at least a poor solvent for the polymer. Such a polymer solution is then coated on the substrate, and dried under controlled conditions. The lower boiling solvent evaporates more readily and the coating becomes enriched in the liquid which is a poor solvent or nonsolvent. As evaporation proceeds, under proper conditions, the polymer forms as a porous layer. Many different polymers can be used, singly or in combination, for preparing porous blush polymer layers for use in this invention. Typical examples include polycarbonates, polyamides, polyurethanes and cellulose esters such as cellulose acetate. For layers such as those containing a labeled conjugate or other reagent, a coating solution or dispersion including the matrix and incorporated active materials can be prepared, coated as discussed herein and dried to form a dimensionally stable layer.

The thickness of any layer and its degree of permeability are widely variable and depend on actual usage. Dry thickness of from about 5 microns to 100 microns have been convenient, although more widely varying thickness may be preferable in certain circumstances. For example, if comparatively large amounts of interactive material, e.g., polymeric materials like enzymes, are required, it may be desirable to prepare slightly thicker layers.

It can also be desirable to include within a carrier member one or more reflective layers, optionally absorptive to detecting radiation, such as to facilitate signal detection by reflection radiometry, e.g., reflection photometry or a similar technique. Such reflector can be provided by one of the above-described layers or it can be provided by an additional layer that may not have an additional function within the element. Reflective pigments, such as titanium dioxide and barium sulfate, can be used to advantage in a reflecting layer. Blush polymers can also constitute a suitable reflecting material. In one preferred aspect, blush polymer layers can also incorporate a pigment to enhance reflectivity or other functions. The amount of pigment that can be included in a layer together with a blush polymer is highly variable, and amounts of from about 1 to about 10 parts by weight of pigment per part by weight of blush polymer are preferred, with from about 3 to about 6 parts pigment per part of blush polymer being most preferred.

It can be advantageous to incorporate one or more surfactant materials, such as anionic and non-ionic surfactant materials, in the layers of the carrier member. They can, for example, enhance coatability of layer formulations and enhance the extent and range of wetting in layers that are not easily wetted by liquid samples in the absence of an aid such as a surfactant. In layers of the carrier it can also be desirable to include materials that can render nonactive in the analysis of choice, by chemical reaction or otherwise, materials potentially deleterious to such analysis.

As mentioned previously herein, the integral analytical elements can be self-supporting or coated on a support. The support can be opaque or transparent to light or other energy. A support of choice for any particular carrier member will be compatible with the intended mode of signal detection. Preferred supports include transparent support materials capable of transmitting electromagnetic radiation of a wavelength within the region between about 200 nanometers (nm) and about 900 nm. The support need not, of course, transmit over the entire 200-900 nm region, although for fluorometric detection of analytical results through the support it is desirable for the support to transmit over a wider band or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

DETECTABLE RESPONSE

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample.

The term "detectable species", and similar terms as used herein, refer to atoms, chemical groups (i.e., a portion of a molecule) or chemical compounds that are themselves directly or indirectly detectable and the term "detectable response", and similar terms as used herein, refer to the detectable manifestation of the presence of such species. Examples are electromagnetic radiation signals such as fluorescence, phosphorescense, chemiluminescence, a change in light absorption, or reflectance in the visible spectrum thereby producing a visible color change, a change in light absorption or reflectance outside the visible range such as the ultraviolet or infrared. As will be apparent to one skilled in the art of immunoassays, the phrase "detectable response", as used herein, is intended in its broadest sense. In addition to electromagnetic radiations signals the term "detectable response" is also meant to include any observable change in a system parameter, such as a change in or appearance of a reactant, observable precipitation of any component in the test sample or a change in any other parameter, whether it be in the immunoassay system or the test sample. Such other detectable responses include electrochemical responses and colorimetric responses. Moreover, the detectable response is one which can be observed through the senses directly or by use of ancillary detection means, such as a spectrophotometer, ultraviolet light-sensing equipment, fluorometer, spectrofluorometer, pH meter and other sensing means. Desirably, such detectability can be conveniently imparted to the full amount of detectable species without affecting the amount of diffusible product resulting from the analyte interactions which are the basis of the intended analysis.

After the analytical result is obtained as a detectable change, it is measured, usually by passing the test element through a zone in which suitable apparatus for reflection, transmission or fluorescence photometry is provided. Such apparatus serves to direct a beam of energy, such as light, through, in one embodiment, the support. The light is then reflected from the element back to a detecting means or passes through the element to a detector in the case of transmission detection. In a preferred mode, the analytical result is detected in a region of the element totally within the region in which such result is produced. Use of reflection spectrophotometry can be advantageous in some situations as it effectively avoids optical interference from any residues, such as blood cells or urine sediment, which have been left on or in the layers of the element or from atypical urine colors. Conventional techniques of fluorescence spectrophotometry can also be employed if desired. Furthermore, transmission techniques can be used to detect and quantify the indicating reaction products by reacting a flow of radiant energy, for example, ultraviolet, visible or infrared radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of a standard solution of the ligand under assay can be applied adjacent to the area where the drop of sample is placed in order to permit the use of differential measurements in the analysis.

EXAMPLES

The following examples describe experiments which were performed in developing the present invention. While they illustrate preferred embodiments, they are in no way to be interpreted as limiting the scope of the invention.

EXAMPLES 1-2

Aminoglycoside Antibiotic Assays

In aminoglycoside antibiotic assays according to the present invention a labeled conjugate is used wherein the binding component is the antibiotic under assay or a binding analog thereof. A schematic representation of the principles of a competitive binding type of homogeneous immunoassay for a drug is shown in FIG. 1 of the drawings. In assays where antibody is used as the binding partner it has been found that other aminoglycoside antibiotics can cross-react with the antibody for the antibiotic under assay. Thus such other antibiotics qualify as binding analogs and may be used to form the labeled conjugate. Further, the antibody qualifies as reagent for use in assays for the cross-reacting antibiotic. For example, in an assay for gentamicin it has been found that with appropriate antiserum the binding component in the labeled conjugate can be gentamicin itself or sisomicin which cross-reacts. Thus, gentamicin antiserum and a labeled sisomicin conjugate could be used in an assay for gentamicin. Specificity problems are not encountered in clinical situations because it would be known what antibiotic was administered and only one aminoglycoside antibiotic is administered at a time.

The $\beta$-galactosyl-umbelliferone-labeled conjugates formed are of the formula:

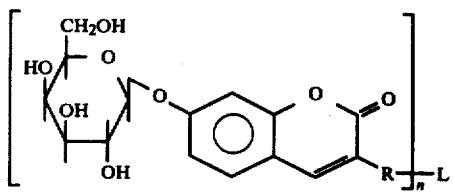

wherein R is a linking group as described hereinbefore terminating in an amino-linking group, preferably carbonyl; L is an aminoglycoside antibiotic coupled by a covalent bond to the linking group R through a primary amino group therein; and n equals 1 to the total number of primary amino groups in the selected antibiotic, inclusive.

Example 1-Gentamicin Assay

Conjugate Preparation

The reaction sequence for the preparation of the glycone-dye-drug conjugate is given in FIG. 2 in the drawings. 3-carboethoxy-7-hydroxycoumarin (II) was prepared by a Knoevenagel condensation of 2,4-dihydroxybenzaldehyde (Aldrich Chemical Co., Milwaukee, Wis., USA) with diethylmalonate in acetic acid, benzene, and piperidine as described in *J. Am. Chem. Soc.* 63:3452 (1971). The potassium salt of 7-β-galactosylcoumarin-3-carboxylic acid (III) was prepared by the reaction of 3-carboethoxy-7-hydroxycoumarin (II) and 2,3,4,6-tetraacetyl-α-D-galactosyl bromide (I, Sigma Chemical Co., St. Louis. Mo., USA) as described by Leaback for the preparation of methylumbelliferyl-β-D-galactoside in *Clin. Chim. Acta* 12:647 (1965). The potassium salt of this compound was purified by chromatography on silica gel-60 (E. Merck, St. Louis, Mo., USA) with a gradient of n-butanol/methanol/water (4/2/1 by volume) and methanol/water (1/6). After recrystallization from acetone-water, the corrected melting point of the product was 258°-263° C. (decomp.).

Analysis: Calculated for $C_{16}H_{15}O_{10}K$: C, 47,28: H, 3.73; K, 9.62. Found: C, 47.30; H, 3.74; K, 9.34.

$[\alpha]_D = -77.4°$ (c 1.0, $H_2O$),

NMR Spectrum ($D_2O$): δ8.2 (s, 1H), 7.6 (m, 1H), 7.0 (m, 2H), 5.1 (s, 1H), and 4.0 (m, 6H).

Infrared Spectrum (KBr): 1705 $cm^{-1}$ (carbonyl), 1620 $cm^{-1}$ (C=C).

β-Galactosyl-umbelliferone-sisomicin (IV) was prepared by mixing 50 milligrams (mg) (117 μmol) of the potassium salt of 7-β-galactosylcoumarin-3-carboxylic acid (III) with 171 mg of sisomicin sulfate (223 μmol of sisomicin free base, Schering Corp., Bloomfield, N.J., USA) in 2 ml of water. The pH was adjusted to 3.8 by dropwise addition of 1 molar hydrochloric acid. The solution was cooled in an ice bath and 30 mg (150 μmol) of 1-ethyl-3-(3-dimethylaminopropyl)-carbodiimide hydrochloride (Pierce Chemical Co., Rockford, Ill., USA) was added. After 2 hours the mixture was chromatographed at 25° C. on a 2.5×50 centimeter (cm) column of CM-Sephadex C-25 (Pharmacia Laboratories, Inc., Piscataway, N.J., USA) 5.8 ml fractions were collected, and their absorbance was monitored at 345 nanometers (nm). The column was washed with 200 ml of 50 mmol/liter ammonium formate to elute unreacted 7-β-galactosylcoumarin-3-carboxylic acid (III). A linear gradient formed with 400 ml of 50 mmol/liter and 400 ml of 1.8 mol/liter ammonium formate, was applied to the column. A peak of material absorbing at 345 nm eluted at approximately 1.4 mol/liter ammonium formate. After the gradient, the column was washed with 600 ml of 1.8 mol/liter ammonium formate. Three 345 nm absorbing peaks were eluted in this wash. Eluted unreacted sisomicin was well separated from the last 345 nm absorbing peak.

The carbodiimide-activated reaction leads to the formation of amide bonds between the carboxylic acid of β-[7-(3-carboxy-coumarinoxy)]-galactoside and the primary amino groups of sisomicin. The major peak of β-galactosyl-umbelliferone-sisomicin (the last 345 nm absorbing peak) was used in the present studies. Ammonium formate was removed by lyophilization. Because the absorptivity of isolated labeled conjugate is currently unknown, the relative concentration is presented in terms of $A_{345}$ units. One $A_{345}$ unit is the quantity of material contained in 1 ml of a solution that has an absorbance of 1.0 at 345 nm when measured with a 1 cm light path.

Antisera Preparation

Antiserum to gentamicin was prepared as described in *Nature New Biol.* 239:214 (1972).

Element Preparation

A conjugate solution prepared in 5.0 mmol/liter sodium formate (pH 3.5) contained 67.8 micromolar (μm) of the β-galactosyl-umbelliferone-sisomicin conjugate (prepared as referenced above). An antiserum solution, prepared of 10 microliters (μL) of the antiserum (prepared as referenced above) 3.6 μL of water and 4 μL of a 0.5 molar N,N-bis-(2-hydroxyethyl)-glycine (Bicine) buffer (pH 8.2, Nutritional Biochemicals Corp., Cleveland, Ohio, USA), was combined with 1.9 μL of the conjugate solution. This combined solution of conjugate and antiserum was incubated at 25° C. for approximately fifteen (15) minutes. The result was a solution of antibody bound conjugate.

To this solution was added 0.5 μL of a reagent, prepared in 50 mmol/liter Bicine buffer which contained 132.7 Units (U)/ml of β-galactosidase (25 ng Protein/ml, *Escherichia coli*-derived enzyme, Grade IV, Sigma Chemical Co., St. Louis, Mo., USA). One unit (U) of the enzyme was defined as that amount which hydrolyzed 1.0 μmole of o-nitrophenyl-β-D-galactoside per minute of pH 7.2 at 37° C. The enzyme preparation used had a specific activity of 745 U per milligram of protein. The complete solution so prepared was then incubated at 25° C. for fifteen (15) minutes.

Carriers comprised of 1×1 cm pieces of Whatman 31 ET filter paper (Whatman, Inc., Clifton, N.J.) were laminated onto silver Mylar and mounted by double-faced adhesive tape on 8.3×1 cm polystyrene supports. The above prepared solutions were then pipetted onto the carrier surface opposite the silver Mylar. These were dried in a convection oven at 50° C. for 15 minutes.

Final reagent contents per gentamicin immunoassay element were as follows:

| COMPONENT | CONTENT |
| --- | --- |
| Volume Antisera | 10 μL |
| Conjugate | β-gal-umb-sisomicin |
| Quantity | 130.0 picomoles |
| Buffer (bicine) | 2.0 micromoles |
| β-galactosidase | 0.065 Units |
| Sodium formate | 9.5 nanomoles |

Analytical Procedure

The analytical elements which had been prepared and fixed to supports as described above were placed in a chamber suitable for maintaining a constant humidity. Prior to closing the chamber, 70 μL aliquots of drug were pipetted onto the exposed surface of the respective analytical elements.

The fluorescence generated at room temperature at the end of 15 minutes was measured in a fluorometer equipped with a mechanical holder suitable for horizontally positioning the analytical element. The fluorometer had been adjusted to provide an excitation light source at 405 nm, which struck the surface at 90° and to detect light emitted at a wavelength of 450 nm. A front face measurement of fluorescence was made at a 90° angle from the pad.

The concentration ranges assayed were as follows:

| RANGE | GENTAMICIN |
|---|---|
| Therapeutic Range | 1–10 μg/ml |
| Dose Response Range Checked | 0–2.0 μg/ml |

The dose response range checked covers the therapeutic range since solutions containing up to 10 μg/ml were checked after 1:5 dilution in distilled water.

Results

Figure 3:
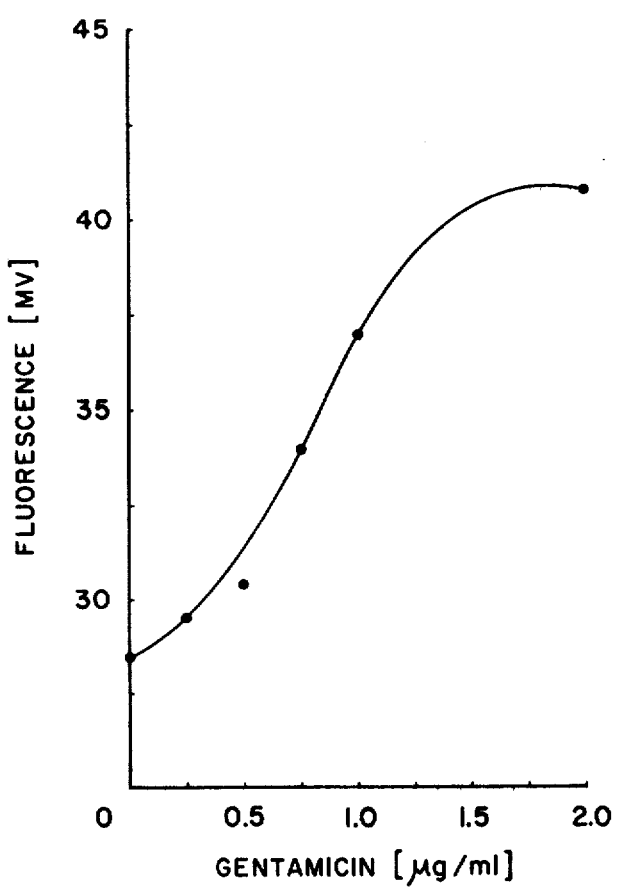

The data obtained by the above-described procedure is graphically illustrated by FIG. 3. The ordinate units are expressed in terms of millivolts (mv). A millivolt is one thousandth of a volt.

Conclusion

The resultant data show that integral analytical elements, prepared according to the invention provide quantitatively detectable signals which are responsive to the concentration ranges of the gentamicin present. Increasing concentrations of gentamicin results in a drug dependent increase in fluorescence of the respective analytical elements. The techniques used in the experiment described have made it possible for all components to be incorporated into a single solution which is incorporated with a carrier to form a single element.

Example II-Tobramycin Assay

Conjugate Preparation

The reaction sequence and methodology for the preparation of the labeled tobramycin conjugate were basically those of Example I.

With 55 mg (135 μmol) of the potassium salt of 7-β-galactosylcoumarin-3-carboxylic acid was mixed 150 mg (220 μmol) of tobramycin (Eli Lilly & Co. Indianapolis, Ind., USA) in 1.5 ml of distilled water. The pH was adjusted to 3.65 by the dropwise addition of 1 N hydrochloric acid and the resulting solution cooled in an ice bath. To initiate the coupling reaction, 30 mg (160 μmol) of 1-ethyl-3(3-dimethylaminopropyl) carbodiimide hydrochloride were added. After overnight incubation of 4° C., two drops of 1 N sodium hydroxide were added to give a pH of 6.1.

The product was purified by chromatography on carboxymethyl Sephadex gel (Pharmacia Laboratories, Inc.) with ammonium formate as eluant. After an initial wash with 0.05 M ammonium formate to remove unreacted galactoside, 1.5 M ammonium formate was used to elute conjugated products. Five peaks of material absorbing at 345 nm were eluted, with the third peak being selected for use in this study.

Antisera Preparation

Antiserum to tobramycin was prepared as described in *Nature New Biol.* 239:214 (1972).

Element Preparation

Preparation of the analytical element was as described in Example 1 with the exception that the conjugate and antiserum used were those prepared as described in this Example.

Final reagent contents per tobramycin immunoassay element were as follows:

| COMPONENT | CONTENT |
|---|---|
| Volume Antisera | 10 μL |
| Conjugate | βgal-umb-tobramycin |
| Quantity | 100.0 picomoles |
| Buffer (bicine) | 2.0 micromoles |
| β-galactosidase | 0.065 Units |
| Sodium formate | 1.7 nanomoles |

Analytical Procedure

The procedure followed in performing the assays reported by this Example were identical with those described in Example 1.

The concentration ranges assayed were as follows:

| RANGE | TOBRAMYCIN |
|---|---|
| Therapeutic Range | 1–10 μg/ml |
| Dose Response Range Checked | 0–0.6 μg/ml |

The dose response range checked includes the therapeutic range after a 1:20 dilution.

Results

Figure 4:
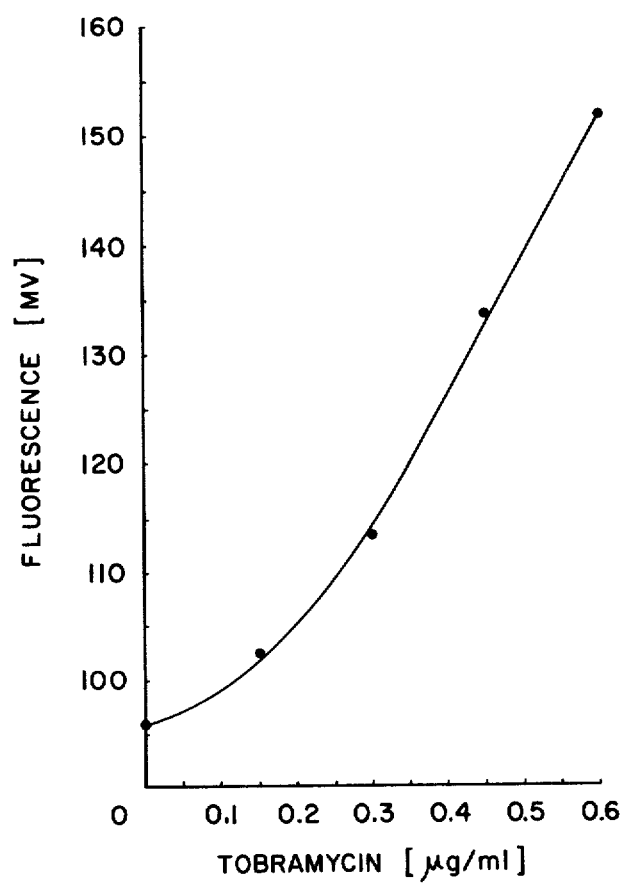

The data obtained by the above-described procedure is graphically illustrated by FIG. 4. The ordinate units are expressed in terms of electrical output.

Conclusion

The resultant data show that integral analytical elements, prepared according to the invention, provide quantitatively detectable signals which are responsive to the concentration ranges of the tobramycin present. Increasing concentrations of tobramycin results in a drug dependent increase in fluorescence of the respective analytical elements. The techniques used in the experiment described have made it possible for all components to be incorporated into a single solution which is incorporated with a carrier to form a single element.

Example III-Theophylline Assay

Theophylline [1,3-dimethylxanthine, cf. *The Merck Index*, 9th ed., p. 1196 (1976)] is a drug useful in the management of asthma. In most patients, the therapeutic range of serum concentration lies between 10 and 20 μg/ml whereas toxicity almost invariably appears at blood levels over 35 μg/ml.

Figure 5:
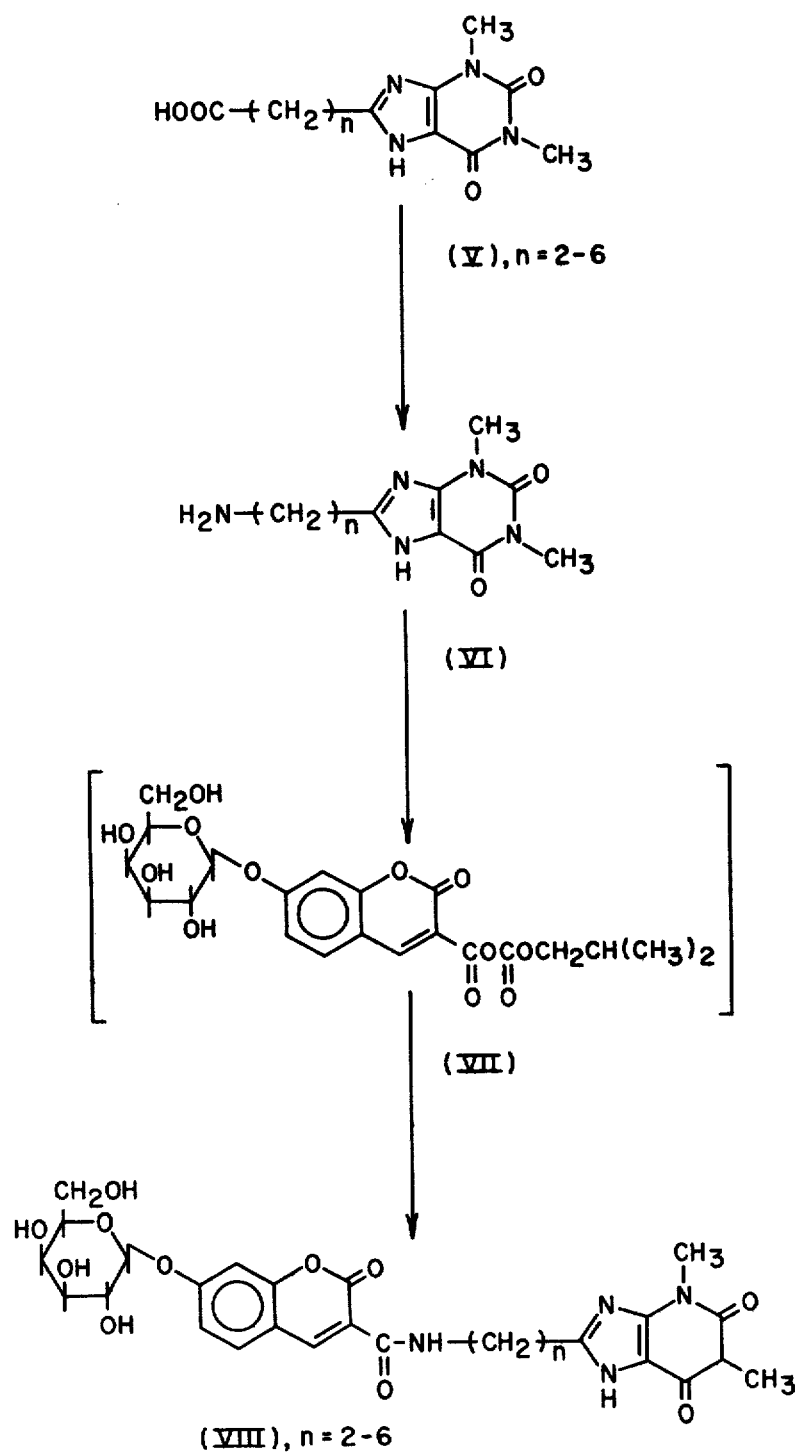

Conjugate Preparation

β-galactosyl-umbelliferone-labeled theophylline conjugates are prepared according to the reaction scheme shown in FIG. 5. This synthetic route is exemplified by the following method of preparing 8-[3-(7-β-galactosyl-coumarin-3-carboxamido)propyl]theophylline (VIII), n=3.

8-(3-Aminopropyl)theophylline (II)

A mixture of 2.66 g (0.01 mol) of 8-(3-carboxypropyl)theophylline (V) [Cook et al, *Res. Commun. Chem. Path. Pharmacol.* 13(3):497–505 (1976)], 20 ml of chloroform, and 3 ml of concentrated sulfuric acid was stirred at 50° C. under an argon atmosphere. To this was added 1.3 g of solid sodium azide portionwise over a 90 minute period [cf. *Organic Reactions* 47:28 (1967)]. The reaction was cooled and the solvent removed under reduced pressure. The residue was combined with enough sodium bicarbonate solution to bring the pH to 7.5. Ten grams of celite (Fisher Scientific Co., Pittsburgh, Pa.) was added and the water evaporated. The impregnated celite was placed atop a column of 200 g of silica gel (E. Merck Co., Darmstadt, West Germany) made up in 9:1 (v:v) ethanol-1 molar aqueous triethylammonium bicarbonate. The column was eluted with this solvent and 15 ml fractions were collected. Fractions 171 to 225 were combined and evaporated to give 500 mg of a white powder. This substance was rechromatographed on a column of CM-Sephadex, ammonium form (Pharmacia Fine Chemicals, Piscataway, N.J., USA), eluting with 0.5 molar ammonium bicarbonate. The bed volume was 3 cm by 50 cm; and 10 ml fractions were collected. Fractions 65 to 110 were combined and evaporated to give 250 mg of a white solid. It was taken up in dilute hydrochloric acid, then reevaporated.

The residue was recrystallized from methanol to give 90 mg (3% yield) of the hydrochloric acid salt of (VI) as pale tan needles that did not melt below 300° C.

Analysis: Calculated for $C_{10}H_{16}N_5ClO_2$: C, 43.88; H, 5.89; N, 25.59. Found: C, 43.77; H, 5.88; N, 25.46.

Infrared Spectrum (KCl): 1695 cm$^{-1}$ and 1655 cm$^{-1}$ (amide carbonyls).

8-[2-(7-$\beta$-galactosylcoumarin-3-carboxamide)propyl]-theophylline (VIII)

A reaction mixture was prepared containing 24 g of potassium hydroxide, 80 ml of water, 240 ml of methanol and 20 g (0.035 mmol) of ethyl 7-$\beta$-galactosylcoumarin-3-carboxylate [Burd et al, *Clin. Chem.* 23:1402 (1977)]. The reaction was stirred at 50° C. for 15 hours. When cool, the methanol was removed under reduced pressure. The concentrated aqueous solution was acidified to pH 2.0 with concentrated hydrochloric acid. The white precipitate was collected, washed with cold water, and recrystallized from hot water. The crystals were collected, washed with acetone, and dried at 80° C. for 1 hour. This gave 12 g of 7-$\beta$-galactosylcoumarin-3-carboxylic acid as white crystals, mp 250°-255° C.

A mixture of 1.45 g (0.004 mol) of 7-$\beta$-galactosylcoumarin-3-carboxylic acid, 404 mg (0.004 mol) of triethylamine, and 40 ml of dry dimethyl formamide (DMF) was cooled to −10° C. while stirring under argon. To this was added 546 mg (0.004 mol) of isobutyl chloroformate (Aldrich Chemical Co., Milwaukee, Wis.) to form the mixed anhydride (VII). Ten minutes later, an additional 404 mg of triethylamine and 949 mg (0.004 mol) of 8-(3-aminipropyl)theophylline (VI) was added to the flask. After stirring for 30 minutes at −10° C., the reaction was allowed to warm to room temperature. It was combined with 10 g of silica gel and the DMF removed under high vacuum. The impregnated silica gel was placed atop a column of 170 g of silica gel and the column eluted with anhydrous ethanol and collecting 15 ml fractions. Fractions 41 to 475 were combined and evaporated to give 545 mg of a yellow solid. It was dissolved in water, filtered, and concentrated to a 20 ml volume. A small amount of precipitate formed and was discarded. The filtrate was chromatographed on a 2.5 cm by 57 cm column of Sephadex LH-20 gel (Pharmacia Fine Chemicals, Piscataway, N.J.), eluting with water and collecting 15 ml fractions. Fractions 18 to 23 were combined, evaporated, and residue recrystallized from water to give 55 mg (2% yield) of the labeled conjugate (VIII) as a light yellow solid, mp 190°-192° C.

Analysis: Calculated for $C_{26}H_{29}N_5O_{11}$: C, 53.15; H, 4.98; N, 11.92. Found: C, 52.65; H, 5.01; N, 11.80.

The above-described synthesis of the $\beta$-galactosyl-coumarin-theophylline conjugate (VIII), n=3, can be modified to yield labeled conjugates wherein n=2 through 6 by replacing the starting material 8-(3-carboxypropyl)theophylline (V), n=3, with the appropriate 8-($\omega$-carboxyalkyl)theophylline as follows:

| n | alkylene |
|---|----------|
| 2 | ethylene |
| 4 | butylene |
| 5 | pentylene |
| 6 | hexylene |

Antiserum Preparation

Antiserum was collected from rabbits immunized with a theophylline immunogen conjugate prepared as described by Cook et al, *Res. Comm. Chem. Path. Pharmacol.* 13:497-505 (1976).

Element Preparation

Preparation of the analytical element was as described in Example 1 with the exception that the conjugate and antiserum used were those prepared as described in this Example and that the conjugate was dissolved in dimethylsulfoxide (DMSO) rather than formate.

Final reagent contents per theophylline immunoassay element were as follows:

| COMPONENT | THEOPHYLLINE |
|-----------|--------------|
| Volume Antisera | 10 $\mu$L |
| Conjugate | $\beta$-gal-umb-theophylline |
| Quantity | 129.9 picomoles |
| Buffer (bicine) | 2.0 micromoles |
| $\beta$-galactosidase | .065 Units |
| DMSO | 0.17 $\mu$L |

Analytical Procedure

The procedure followed in performing the assays reported by this Example were identical with those described in Example 1.

The concentration ranges assay were as follows:

| RANGE | THEOPHYLLINE |
|-------|--------------|
| Therapeutic Range | 10–20 $\mu$g/ml |
| Dose Response | 1–4.0 $\mu$g/ml |
| Range Checked | |

The dose response range checked includes the therapeutic range after a 1:40 dilution.

Results

Figure 6:
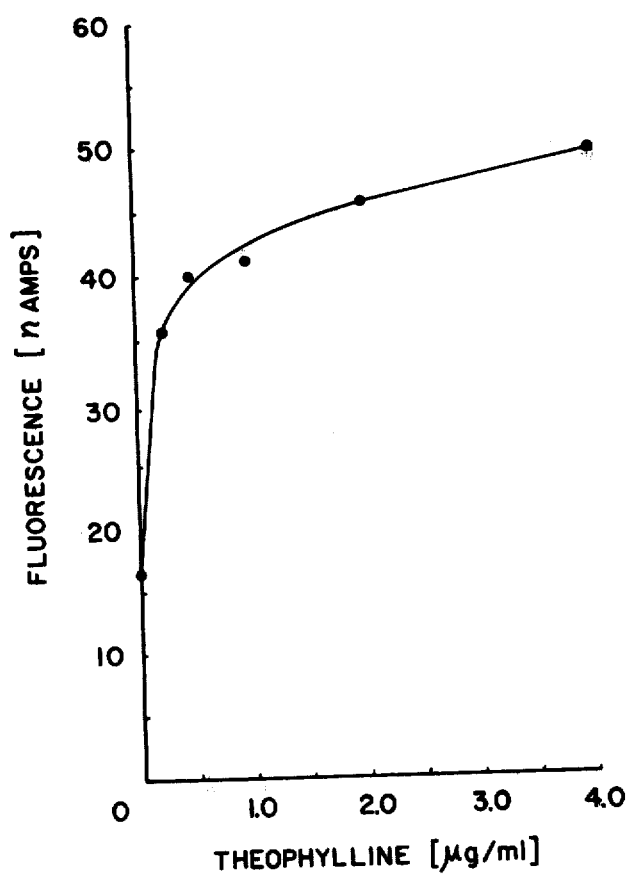

The data obtained by the above-described procedure is graphically illustrated by FIG. 6. The ordinate units are expressed in terms of nanoampers (namps). A nanoampere is one billionth of an ampere.

Conclusion

The resultant data show that integral analytical elements, prepared according to the invention provide quantitatively detectable signals which are responsive to the concentration ranges of the theophylline present. Increasing concentrations of theophylline results in a drug dependent increase in fluorescence of the respective analytical elements. The techniques used in the experiment described have made it possible for all components to be included in a single solution which is incorporated with a carrier to form a single element.

Example IV-Carbamazepine Assay

Carbamazepine [5H-dibenz[b,f]azepine-5-carboximde, cf. *The Merck Index*, 9th ed., p. 226 (1976)], sold under various trademarks including Tegretol, is an anticonvulsant drug useful in the management of epilepsy. The therapeutic range of serum concentration in most patients lies between 4 and 12 $\mu g/ml$ whereas toxic signs may appear at blood levels over 12 $\mu g/ml$.

Figure 7:
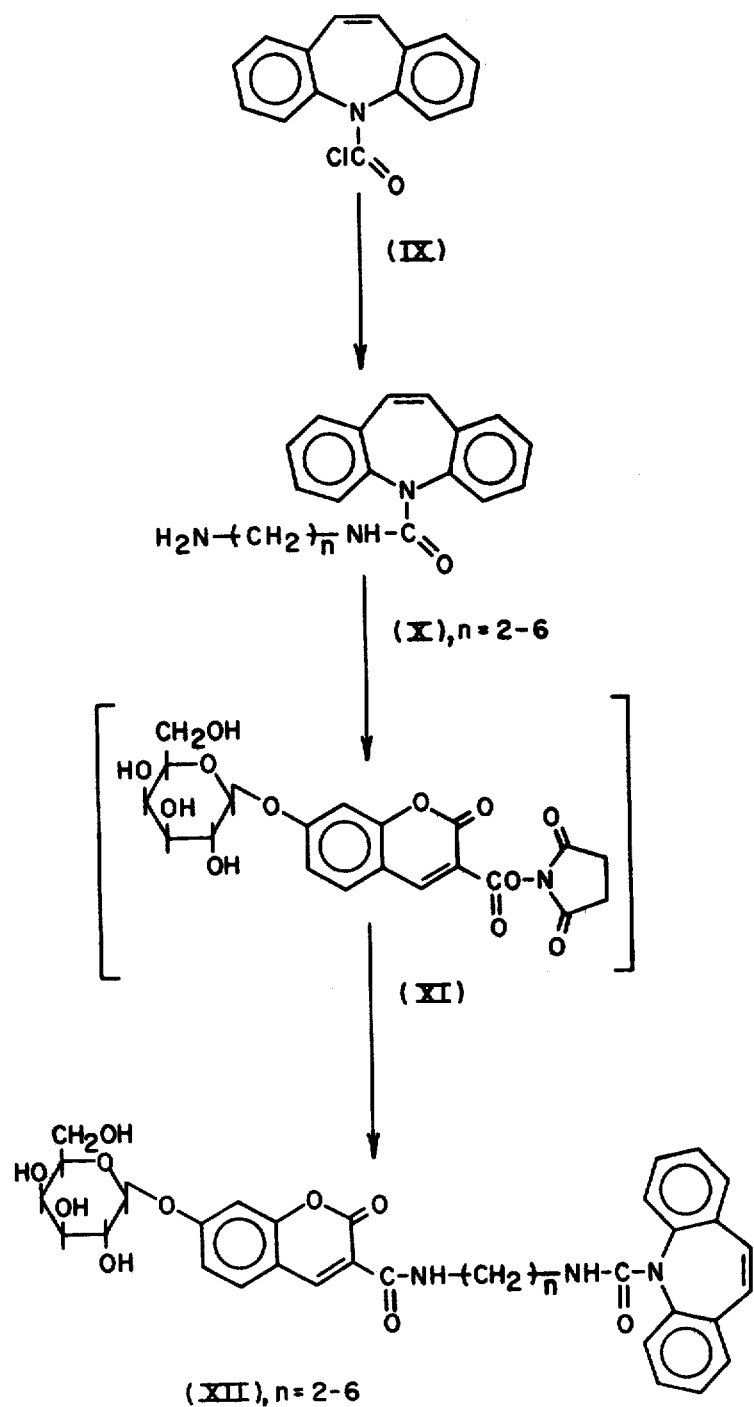

Conjugate Preparation $\beta$-galactosyl-umbelliferone-labeled carbamazepine conjugates are prepared according to the reaction scheme shown FIG. 7 in the drawings. This synthetic route is exemplified by the following method of preparing N-[4-(7-$\beta$-galactosylcoumarin-3-carboxamido)-butyl]aminocarbonyl-5H-dibenz[b,f]azepine (XII), n=4.

N-(4-Aminobutyl)aminocarbonyl-5H-dibenz[b,f]azepine (X)

Phosgene gas was bubbled into a room temperature suspension of 14.1 g (0.073) of 5H-dibenz[b,f]azepine (Aldrich Chemical Co., Milwaukee, Wis.) in 180 ml of dry toluene until 15 g was absorbed. The warm mixture was stirred for 2 hours, heated at reflux for 2 hours, then stirred at room temperature overnight. The yellow solution, now containing N-chlorocarbonyl-5H-dibenz[b,f]azepine (IX), was concentrated by boiling to about 100 ml volume. It was added dropwise over 1 hour to a solution at room temperature of 26 g (0.29 mol) of 1,4-diaminobutane in 250 ml of toluene. A white crystalline solid began to precipitate immediately. After the addition was complete, the resulting slurry was stirred at reflux for 3 hours. It was then cooled, filtered, and the precipitate washed with toluene. The filtrate was evaporated and excess butane diamine was removed by heating to 100° C. at 0.2 mm. The residual oil was taken up in dilute hydrochloric acid and some insoluble material filtered off. The solution was made basic to pH 9.5 with sodium carbonate and extracted with chloroform. Evaporation of this extract gave a glass that solidified when triturated with ether. This gave 15.8 g (70% yield) of the amine (X), as a solid, mp 114°–116° C.

Analysis: Calculated for $C_{19}H_{21}N_3O$: C, 74.24; H, 6.89; N, 13.67. Found: C, 73.92; H, 6.71; N, 13.64.

Infrared Spectrum (KCl); 1655 cm$^{-1}$ (amide carbonyl). ·

N-[4-(7-$\beta$-Galactosylcoumarin-3-carboxamido)butyl]-aminocarbonyl-5H-dibenz[b,f]azepine (XII)

A mixture of 24 g of potassium hydroxide, 80 ml of water, 240 ml of methanol, and 20 g (0.035 mol) of ethyl 7-$\beta$-galactosylcoumarin-3-carboxylate [Burd et al, *Clin. Chem.*] was prepared. The methanol was removed under reduced pressure. The concentrated aqueous solution was acidified to pH 2.6 with concentrated hydrochloric acid. The white precipitate was collected, washed with cold water, and recrystallized from hot water. The crystals were collected, washed with acetone, and dried at 80° C. for 1 hour. This gave 12 g (54% yield) of 7-$\beta$-galactosylcoumarin-3-carboxylic acid as white crystals, mp 250°–255° C.

A mixture of 1.02 g (5 mmol) of dicyclohexylcarbodiimide, 575 mg (5 mmol) of N-hydroxysuccinimide, and 50 ml of dry dimethylformamide (DMF) was stirred at room temperature under argon for 30 minutes. The clear, colorless solution was cooled to −5° and 1.835 g (5 mmol) of 7-$\beta$-galactosylcoumarin-3-carboxylic acid was added. The reaction was allowed to warm to room temperature and stirred for 2 hours. The mixture was then cooled in an ice bath and the precipitate of dicyclohexyl urea removed by filtration under argon. The filtrate, now containing the N-hydroxysuccinimide ester (XI), was combined with 1.54 g (5 mmol) of N-(4-aminobutyl)aminocarbonyl-5H-dibenz[b,f]azepine (X) dissolved in 5 ml of DMF. The reaction was stirred overnight at room temperature. The solvent was removed at 50° C./12 mm on the rotary evaporator and the residue triturated with dilute aqueous sodium bicarbonate solution. The insoluble material was chromatographed on 100 g of silica gel (E. Merck Co., Darmstadt, West Germany) eluting with a gradient of 2 L of ethyl acetate to 2 L of ethanol and 20 ml fractions were collected. Fractions 190 to 250 were combined, evaporated, and the residue recrystallized twice from ethanol. This gave 1.0 g (30% yield) of the labeled conjugate (XII) as a white powder, mp 150°–160° C. (decomposed).

Analysis: Calculated for $C_{35}H_{35}N_3O_{10}$: C, 63.95; H, 5.35; N, 6.39. Found: C, 63.55; H, 5.77; N, 6.14.

Mass Spectrum (field desorption): m/e 658, [P+1].

Optical Rotation: $[\alpha]_D = -46.84°$ (c 1.0, MeOH)

The above-described synthesis of the $\beta$-galactosylcoumarin-carbamazepine conjugate (XII), n=4, can be modified to yield labeled conjugates wherein n=2 through 6 by replacing the starting material 1,4-diaminobutane with the appropriate $\alpha,\omega$-diaminoalkane as follows:

| n | $\alpha,\omega$-diaminoalkane |
|---|---|
| 2 | ethylenediamine |
| 3 | 1,3-diaminopropane |
| 5 | 1,5-diaminopentane |
| 6 | 1,6-diaminohexane |

Antiserum Preparation

Antiserum was obtained by immunization of rabbits with carbamazepine-bovine serum albumin immunogen conjugate.

Element Preparation

Preparation of the analytical element was as described in Example 1 with the exception that the conjugate and antiserum used were those prepared as described in this Example and that the conjugate was dissolved in DMSO.

Final reagent contents per carbamazepine immunoassay element were as follows:

| COMPONENT | CARBAMAZEPINE (CBZ) |
|---|---|
| Volume Antisera | 10 $\mu L$ |
| Conjugate | $\beta$-gal-umb-CBZ |
| Quantity | 112.3 picomoles |
| Buffer (bicine) | 2.0 micromoles |
| $\beta$-galactosidase | .065 Units |
| DMSO | 0.17 $\mu L$ |

Analytical Procedure

The procedure followed in performing the assays reported by this Example were identical with those described in Example 1.

The concentration ranges assayed were as follows:

| RANGE | CARBAMAZEPINE |
|---|---|
| Therapeutic Range | 4–12 µg/ml |
| Dose Response Range Checked | 0–0.4 µg/ml |

The dose response range checked includes the therapeutic range after a 1:50 dilution.

Results

Figure 8:
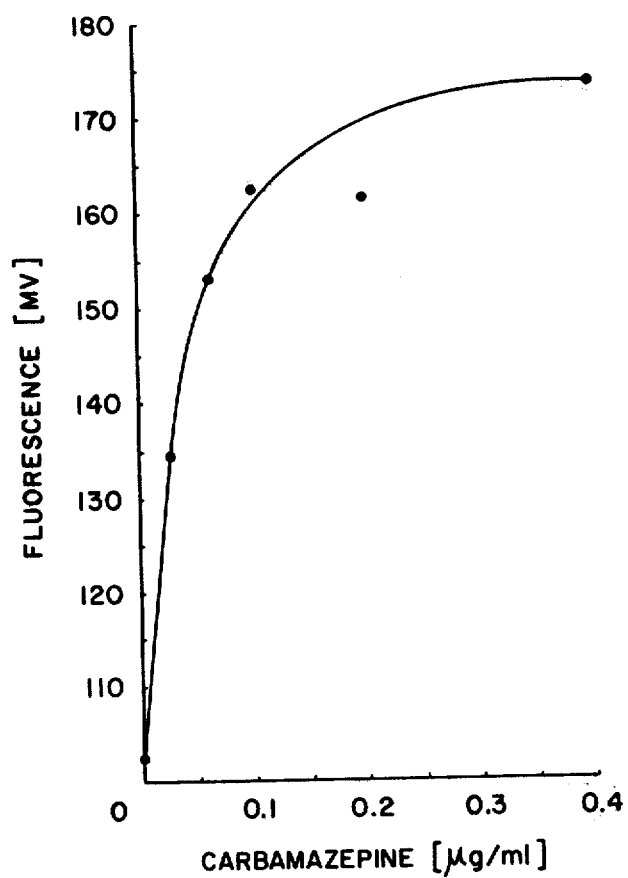

The data obtained by the above-described procedure is graphically illustrated by FIG. 8. The ordinate units are expressed in terms of electrical output.

Conclusion

The resultant data show that integral analytical elements, prepared according to the invention, provide quantitatively detectable signals which are responsive to the concentration ranges of the carbamazepine present. Increasing concentrations of carbamazepine result in a drug dependent increase in fluorescence of the respective analytical elements. The techniques used in the experiment described have made it possible for all components to be combined in a single solution which is incorporated with a carrier to form a single element.

What is claimed is:

1. A test device for detecting the presence of a ligand in a test sample, said test device comprising a carrier matrix incorporated with components for a homogeneous specific binding assay for the ligand, said components comprising a complex of a specific binding partner for the ligand and a conjugate comprising a label and the ligand or a specific binding analog of the ligand, wherein the label is capable of providing a detectable response when not part of said complex, but which response is inhibited when the label-containing conjugate is part of said complex, and wherein said specific binding partner is unbound to said matrix.

2. The device of claim 1 in which said label comprises a prosthetic group of an enzyme and in which said components further comprise an apoenzyme of said enzyme.

3. The device of claim 1 in which said label comprises an enzyme substrate, and in which said components further comprise an enzyme capable of acting on said substrate to produce a detectable response.

4. The device of claim 1 in which said label comprises a coenzyme, and in which said components further comprise reactants for an enzymatic reaction requiring the participation of said coenzyme.

5. The device of claim 1 in which said label comprises an enzyme modulator, and in which said components further comprise reagents for an enzymatic reaction capable of being modulated by said label.

6. The device of claim 1 in which said label is an enzyme whose activity is affected when the labeled conjugate is complexed with said specific binding partner.

7. The device of claim 1 in which said label is a quenchable fluorescer whose fluorescence is at least partially quenched when the labeled conjugate is complexed with said specific binding partner.

8. The device of claim 1 in which said label is a chemically excitable fluorescer whose ability to be chemically excited is affected when the labeled conjugate is complexed with said specific binding partner.

9. The device of claim 1 in which said label is a double antibody steric hindrance label whereby the activity of said label is hindered when the labeled conjugate is complexed with said specific binding partner.

10. The device of claim 1 in which said label is $\beta$-galactosyl-umbelliferone, and in which said components further comprise $\beta$-galactosidase.

11. The device of any one of claims 1–10 in which said ligand is a polypeptide, protein, carbohydrate, glycoprotein, nucleic acid or sequence thereof, steroid, other molecule for which a specific binding partner exists or can be synthesized, or a specific binding analog thereof.

12. The device of claim 11 wherein the ligand is an immunoglobulin, enzyme, hapten having a molecular weight between 100 and 1,500, aminoglycoside, antibiotic, hormone, vitamin, steroid, nucleic acid, or nucleic acid sequence.

13. A method for preparing a test device for detecting the presence of a ligand in a test sample, said method comprising the steps of
forming a complex of a specific binding partner for said ligand and a conjugate comprising a label and the ligand or a specific binding analog of the ligand, wherein the label is capable of providing a detectable response when not part of said complex, but which response is inhibited when the label-containing conjugate is part of said complex, and
contacting a carrier with said complex, thereby incorporating said carrier with said complex.

* * * * *